US009089401B2

(12) United States Patent
Raksi et al.

(10) Patent No.: US 9,089,401 B2
(45) Date of Patent: Jul. 28, 2015

(54) ADJUSTING OPHTHALMIC DOCKING SYSTEM

(75) Inventors: Ferenc Raksi, Mission Viejo, CA (US); Wesley William Lummis, Oceanside, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 966 days.

(21) Appl. No.: 13/102,208

(22) Filed: May 6, 2011

(65) Prior Publication Data

US 2012/0283708 A1    Nov. 8, 2012

(51) Int. Cl.
*A61B 18/18*   (2006.01)
*A61F 9/009*   (2006.01)
*A61F 9/008*   (2006.01)

(52) U.S. Cl.
CPC ....... *A61F 9/009* (2013.01); *A61F 2009/00851* (2013.01); *A61F 2009/00872* (2013.01); *A61F 2009/00887* (2013.01); *A61F 2009/00897* (2013.01)

(58) Field of Classification Search
CPC ......... A61F 9/007; A61F 9/008; A61F 9/009; A61F 2009/00861; A61F 2009/00872
USPC .......................................... 606/3–6, 166–171
See application file for complete search history.

(56) References Cited

U.S. PATENT DOCUMENTS

| | | |
|---|---|---|
| 3,706,304 A | 12/1972 | Sisler |
| 4,367,018 A | 1/1983 | Abe |
| 4,453,546 A | 6/1984 | Katz et al. |
| 4,600,008 A | 7/1986 | Schmidt |
| 4,718,418 A | 1/1988 | L'Esperance, Jr. |
| 4,753,526 A | 6/1988 | Koester |
| 4,905,711 A | 3/1990 | Bennett et al. |
| 4,907,586 A | 3/1990 | Bille et al. |
| 4,964,717 A | 10/1990 | Koester |
| 4,994,058 A | 2/1991 | Raven et al. |
| 5,108,412 A | 4/1992 | Krumeich et al. |
| 5,112,328 A | 5/1992 | Taboada et al. |
| 5,196,027 A | 3/1993 | Thompson et al. |
| 5,226,903 A | 7/1993 | Mizuno |
| 5,252,998 A | 10/1993 | Reis et al. |
| 5,280,491 A | 1/1994 | Lai |

(Continued)

FOREIGN PATENT DOCUMENTS

| | | |
|---|---|---|
| CA | 2128104 A1 | 7/1993 |
| EP | 0627207 | 12/1994 |

(Continued)

OTHER PUBLICATIONS

European Supplementary Search Report for European Application No. 087994331 with mailing date Feb. 13, 2013, 6 pages.

(Continued)

*Primary Examiner* — Ahmed Farah

(57) ABSTRACT

An adjusting ophthalmic docking system is described that includes a curved contact element, disposed on a procedure eye, a conformation platform at a distal tip of an optical system to support an adjustment of the curved contact element, and a connector to accommodate the adjustment of the contact element. The curved contact element can be a meniscus-shaped contact lens, with a proximal surface radius larger than a distal surface radius. The contact lens can be made of an approximately refractive index-matching material, such as a fluoro-polymer.

21 Claims, 6 Drawing Sheets

(56) References Cited

U.S. PATENT DOCUMENTS

| | | | |
|---|---|---|---|
| 5,311,224 A | 5/1994 | Enomoto | |
| 5,324,281 A | 6/1994 | Muller | |
| 5,336,215 A | 8/1994 | Hsueh et al. | |
| 5,360,424 A | 11/1994 | Klopotek | |
| 5,364,390 A | 11/1994 | Taboada et al. | |
| 5,423,801 A | 6/1995 | Marshall et al. | |
| 5,450,144 A | 9/1995 | Ben Nun | |
| 5,549,632 A * | 8/1996 | Lai | 606/5 |
| 5,656,186 A | 8/1997 | Mourou et al. | |
| 5,861,955 A * | 1/1999 | Gordon | 356/511 |
| 5,871,772 A | 2/1999 | Cantoro | |
| 5,957,832 A | 9/1999 | Taylor et al. | |
| 6,019,472 A | 2/2000 | Koester et al. | |
| 6,090,100 A | 7/2000 | Hohla | |
| 6,143,010 A | 11/2000 | Silvestrini et al. | |
| 6,210,401 B1 | 4/2001 | Lai | |
| 6,254,595 B1 | 7/2001 | Juhasz et al. | |
| 6,342,053 B1 | 1/2002 | Berry | |
| 6,344,040 B1 | 2/2002 | Juhasz et al. | |
| 6,373,571 B1 | 4/2002 | Juhasz et al. | |
| 6,412,334 B1 | 7/2002 | Kral et al. | |
| 6,436,113 B1 | 8/2002 | Burba et al. | |
| 6,451,006 B1 | 9/2002 | Bille | |
| 6,458,141 B1 | 10/2002 | Peyman | |
| 6,579,282 B2 | 6/2003 | Bille et al. | |
| 6,623,476 B2 | 9/2003 | Juhasz et al. | |
| 6,634,753 B1 | 10/2003 | Rozenman | |
| 6,641,577 B2 | 11/2003 | Bille | |
| 6,676,653 B2 | 1/2004 | Juhasz et al. | |
| 6,730,073 B2 | 5/2004 | Bruce | |
| 6,730,074 B2 | 5/2004 | Bille et al. | |
| 6,733,491 B2 | 5/2004 | Kadziauskas et al. | |
| 6,752,778 B1 | 6/2004 | Fiedler et al. | |
| 6,776,824 B2 | 8/2004 | Wen | |
| 6,780,176 B2 | 8/2004 | Hasegawa | |
| 6,863,667 B2 | 3/2005 | Webb et al. | |
| 6,899,707 B2 | 5/2005 | Scholler et al. | |
| 6,905,641 B2 | 6/2005 | Platt et al. | |
| 6,991,629 B1 | 1/2006 | Juhasz et al. | |
| 7,018,376 B2 | 3/2006 | Webb et al. | |
| 7,125,119 B2 | 10/2006 | Farberov | |
| 7,238,176 B2 | 7/2007 | Loesel et al. | |
| 7,244,026 B1 | 7/2007 | Ross, III et al. | |
| 7,285,096 B2 | 10/2007 | Burba et al. | |
| 7,330,275 B2 | 2/2008 | Raksi | |
| 7,371,230 B2 | 5/2008 | Webb et al. | |
| 7,390,089 B2 | 6/2008 | Loesel et al. | |
| 7,402,159 B2 | 7/2008 | Loesel et al. | |
| 7,452,080 B2 | 11/2008 | Wiltberger et al. | |
| 7,452,081 B2 | 11/2008 | Wiltberger et al. | |
| 7,611,507 B2 | 11/2009 | Raksi et al. | |
| 8,070,290 B2 | 12/2011 | Gille et al. | |
| 2001/0021844 A1 | 9/2001 | Kurtz et al. | |
| 2002/0103481 A1 | 8/2002 | Webb et al. | |
| 2002/0103482 A1 | 8/2002 | Scholler et al. | |
| 2003/0153904 A1 | 8/2003 | Patel | |
| 2004/0070761 A1 | 4/2004 | Horvath et al. | |
| 2004/0254568 A1 | 12/2004 | Rathjen | |
| 2005/0143718 A1 | 6/2005 | Rathjen | |
| 2005/0154408 A1 | 7/2005 | Dybbs | |
| 2006/0179992 A1 | 8/2006 | Kermani | |
| 2006/0195078 A1 | 8/2006 | Webb et al. | |
| 2006/0261502 A1 | 11/2006 | Platt et al. | |
| 2007/0093795 A1 * | 4/2007 | Melcher et al. | 606/10 |
| 2007/0093796 A1 | 4/2007 | Raksi et al. | |
| 2007/0173791 A1 | 7/2007 | Raksi | |
| 2007/0253083 A1 | 11/2007 | Muhlhoff et al. | |
| 2008/0071254 A1 | 3/2008 | Lummis et al. | |
| 2008/0194915 A1 | 8/2008 | Blackhurst et al. | |
| 2009/0069794 A1 | 3/2009 | Kurtz | |
| 2009/0137989 A1 * | 5/2009 | Kataoka | 606/5 |
| 2009/0163898 A1 | 6/2009 | Gertner et al. | |
| 2009/0182310 A1 | 7/2009 | Gertner et al. | |
| 2011/0166535 A1 | 7/2011 | Hasegawa et al. | |
| 2011/0190739 A1 | 8/2011 | Frey et al. | |
| 2011/0319873 A1 | 12/2011 | Raksi et al. | |

FOREIGN PATENT DOCUMENTS

| | | |
|---|---|---|
| EP | 0536951 B1 | 8/1997 |
| EP | 0634947 B1 | 12/2001 |
| EP | 1982640 | 10/2008 |
| WO | 8803396 A1 | 5/1988 |
| WO | 8906519 A2 | 7/1989 |
| WO | 2011163507 A2 | 12/2011 |

OTHER PUBLICATIONS

International Search Report for corresponding International Application No. PCT/US2012/049319 with mailing date Nov. 19, 2012, 4 pages.

International Search Report for corresponding International Application No. PCT/US2012/052460 with mailing date Dec. 11, 2012, 6 pages.

Chinn, S. R., et al., Optical coherence tomography using a frequency-tunable optical source, Optics Letters, Mar. 1, 1997, pp. 340-342, vol. 22, No. 5.

Huber, R., et al, Three-dimensional and C-mode OCT imaging with a compact, frequency swept laser source at 1300 nm, Optics Express, Dec. 26, 2005, pp. 10523-15038, vol. 13, No. 26.

International Search Report and Written Opinion dated Mar. 19, 2009 for International Application No. PCT/US2008/075902, filed Sep. 10, 2008, 8 pages.

Yun, S. H., et al., Wavelength-Swept Fiber Laser with Frequency Shifted Feedback and Resonantly Swept Intra-Cavity Acoustooptic Tunable Filter, IEEE Journal of Selected Topics in Quantum Electronics, Aug. 1997, pp. 1087-1096, vol. 3, No. 4.

International Search Report dated Sep. 5, 2012 for corresponding International Application No. PCT/US2012/036546, 3 pages.

International Search Report dated Feb. 29, 2012 for corresponding International Application No. PCT/US2011/041676, 3 pages.

\* cited by examiner

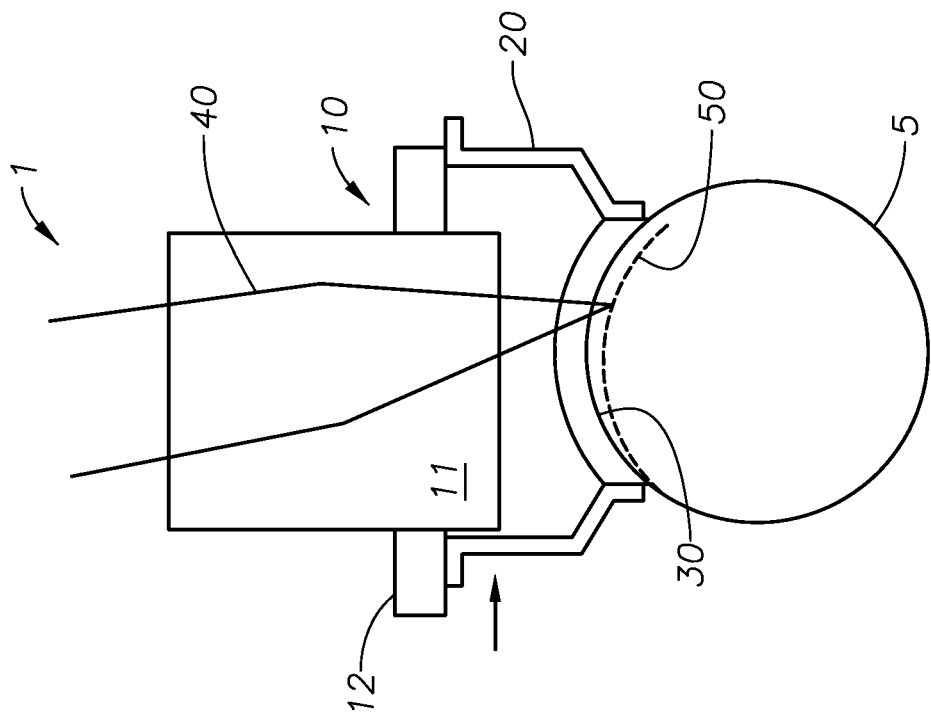
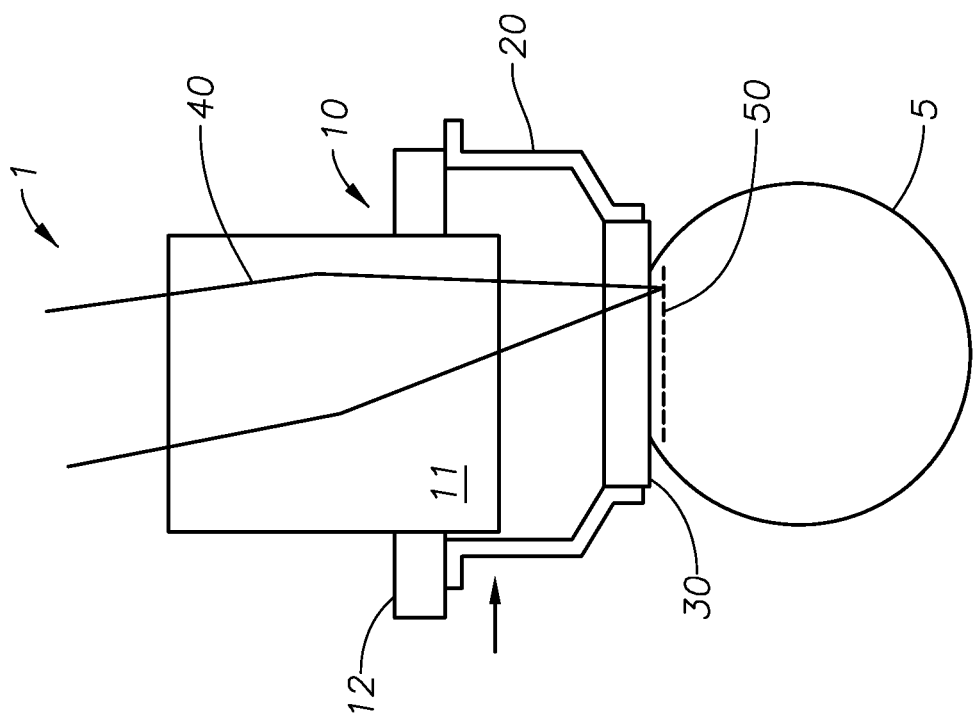

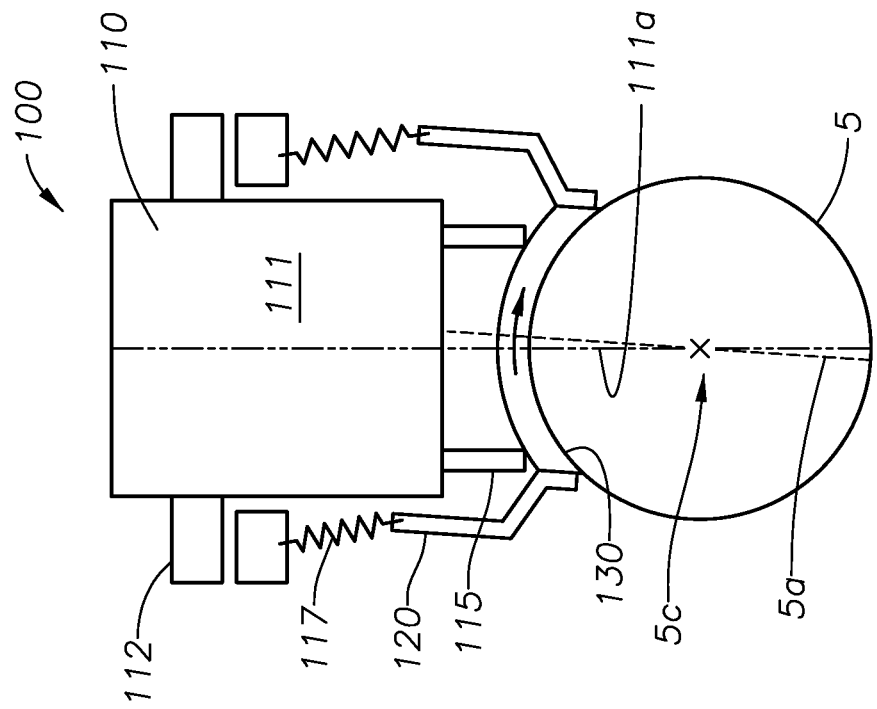
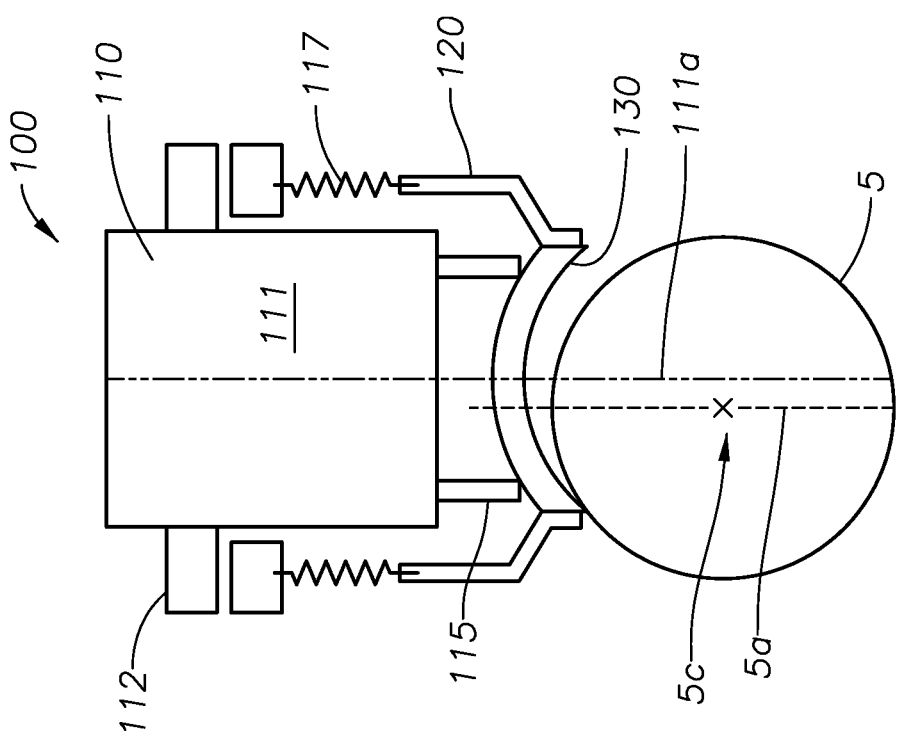
FIG. 3B
FIG. 3C

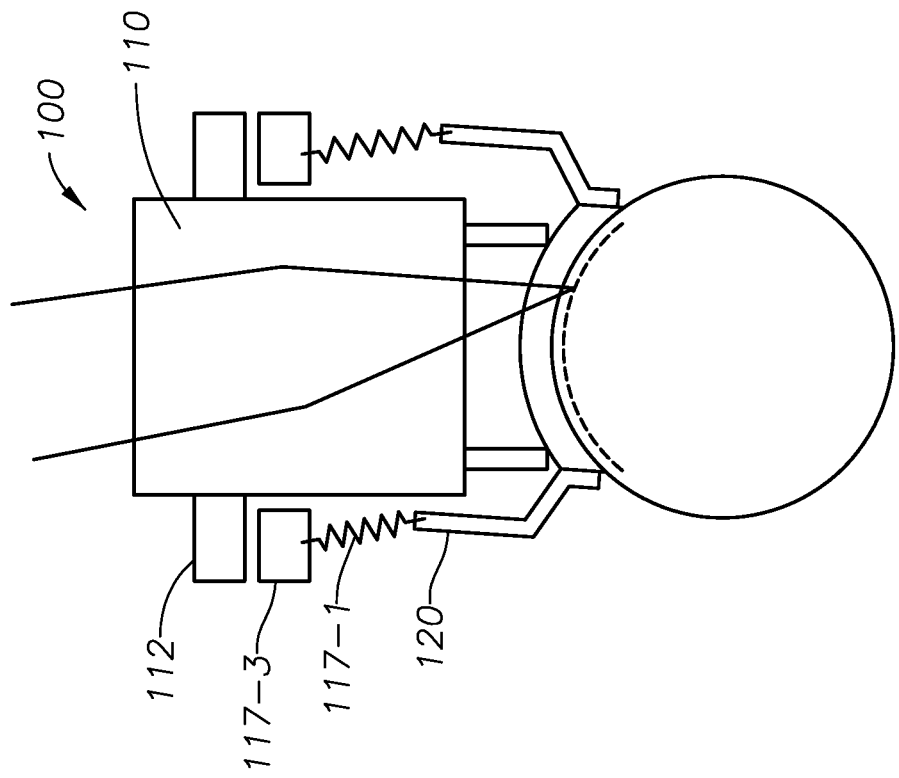
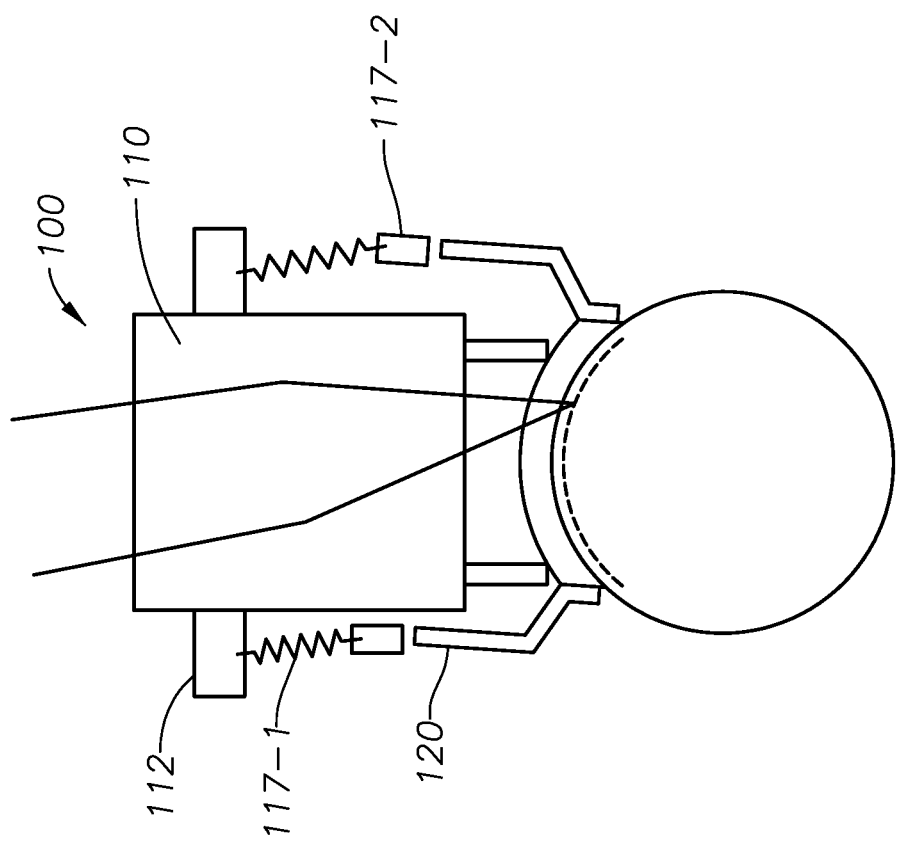

ADJUSTING OPHTHALMIC DOCKING SYSTEM

TECHNICAL FIELD

This patent document describes adjusting patient interfaces. In more detail, this patent document discusses ophthalmic systems with patient interfaces allowing various adjustments of the involved contact lenses.

BACKGROUND

Many ophthalmic surgical laser systems use a patient interface to immobilize the eye the surgery is performed on. A patient interface typically includes a contact lens, directly disposable on the cornea to guide the laser beam into the eye. The contact lens can be affixed to the eye with a vacuum suction ring or skirt that suppresses the motion of the eye relative to the contact lens. Once the contact lens is in place, the laser system scans a surgical laser beam along a selected or predetermined surgical pattern to create cuts in the ophthalmic target tissue.

Some systems employ a one-piece patient interface ("PI") which is rigidly fixed to an objective of the laser system. In others, a two-piece or multi-piece PI is employed, where a top portion of the PI is fixed to the laser system, while a bottom portion is affixed to the eye in preparation for the surgical procedures. Subsequently, the top and bottom portions can be coupled to conveniently align the eye with the objective. Finally, there are laser systems where the structure allows some degree of transverse or lateral movement of the PI relative to the laser system to assist the alignment of the eye.

The surgical patterns are sometimes referenced to the contact lens, sometimes to the objective of the laser system, and in yet other systems, to an internal reference of the laser system. For example, the center of the surgical pattern maybe aligned with the center of the contact lens. Therefore, the precise placement and targeting of the surgical pattern into the eye is critically dependent on the precise docking of the contact lens. As part of the docking, in one piece PIs the contact lens is to be aligned with the optical axis of the eye and with the center of the cornea. In two piece PIs, in addition, once the contact lens is docked in an aligned position to the eye, the top and bottom portion of the PI need to be aligned as well. Finally, in transversely movable PIs, the PI is to assume an essentially central position at the end of docking.

Some laser systems used for corneal procedures, such as LASIK procedures, employ essentially flat or planar, contact lenses. These lenses flatten the cornea when affixed to it with pressure and vacuum suction. Therefore, if the contact lens is docked with a transverse or lateral misplacement to the cornea, the surgical pattern will be placed into the eye with a lateral shift from the center. However, since the cornea itself is flattened, this lateral shift reduces the precision only to a limited degree.

In contrast, in advanced ophthalmic surgical systems the misaligned docking of the contact lens can cause more serious challenges in several aspects.

SUMMARY

In advanced ophthalmic systems, such as in laser systems for cataract surgery, it is advantageous for the surgeon to reduce the deformation of the eyeball, or eye globe by the patient interface. The reasons for this include that planar contact lenses may increase the intra-ocular pressure to undesirable levels. These contact lenses also deform and displace ocular structures such as the lens so that proper placement of the surgical pattern and subsequently of the Intra-Ocular Lens (IOL) can be misguided. Finally, the deformation caused by the patient interface also tends to wrinkle the cornea.

These surgical challenges can be met, for example, by employing a contact lens which has a curvature radius close to that of the cornea. In laser systems with such curved contact lenses, however, even a small misalignment of the contact lens can cause substantial misplacement of the surgical pattern, leading to undesirable surgical outcomes. There can be, in fact two types of misalignments: a misalignment of the curved contact lens with the objective and a misalignment of the curved contact lens with the eye itself.

FIGS. 1A-B and 2A-B illustrate the challenge of curved contact lenses more closely.

FIG. 1A illustrates an ophthalmic docking system 1 with a distal end 10. The distal end 10 often includes an objective 11, containing lenses, and a connecting flange 12. The docking system 1 also can include a patient interface 20 with a contact lens 30. The docking system 1 can guide a laser beam 40 into an eye 5 to form a surgical cut following a surgical pattern 50.

As shown, if the contact lens 30 is docked centered with both the eye and the objective 11 and its optical axis aligned with that of the eye and the objective 11, the surgical pattern 50 will be centered within the eye at its intended position. Throughout the specification the terminology "aligned with the eye" will be used in a broad sense. There are many ways to align the contact lens with the eye: the contact lens can be centered with a pupil, a cornea, or a limbus of the eye. Also, an optical axis of the eye can be defined in several different ways as the eye is not a regular sphere or globe. Some references use the term centration for essentially the same functionality.

FIG. 1B illustrates that if a curved contact lens 30 is employed then the cornea is flattened only moderately or not at all. Accordingly, in a LASIK-type procedure the corneal cut 50 has to be formed as a curved cut at a fixed radial depth, in other words, as a sphere-segment with a fixed radius. This is to be contrasted with systems that flatten the cornea with a flat/planar contact lens, where a fixed depth cut can be formed as a simple flat cut. These flat cuts in flattened corneas spring into their eventual curved shape when the flat contact lens is removed.

Visibly, when the curved contact lens 30 is properly centered, the curved surgical pattern 50 can be placed properly into the eye.

FIGS. 2A-B illustrate the effect of incomplete alignment or centration of the docking process. Here it is noted that the centration involves aligning a center of the contact lens 30 and a center of the eye 5, as well as aligning the center of the contact lens 30 with the center of the laser system, such as its objective 11. A lack of either of these two alignments will be referred to as a "misalignment".

FIG. 2A illustrates the case when, in a transversely movable PI system there is a lateral distance between the center of the eye 5 and center of the distal end 10. In this case the flat contact lens 30 of the transversely movable PI 20 can be docked to the eye 5 properly aligned and centered. However, centering the PI 20 with the eye 5 gives rise to a lateral misalignment of the PI 20 relative to the center of the distal end 10 and to the connecting flange 12, as indicated by the solid arrow.

The PI 20 can be off-center from the distal end 10 for another reason: even before the eye 5 is brought in the proximity of the docking system 1, the PI 20 may have been attached to the distal end 10 with a misalignment that is comparable with the precision required for the placement of a surgical pattern and thus can negatively impact the precision of the docking system 1. For example, the PI 20 can have a flexible attachment portion that has a limited precision of tens of microns, possibly exceeding the precision required for a corneal procedure. Therefore, such a flexible attachment portion can undermine the lateral alignment of the PI 20.

Visibly, if the PI 20 is off-centered for either of the above reasons and a surgical pattern is referenced and centered relative to the objective 11, then it will be placed off the center of the eye and its cornea, resulting in a less than optimal surgical outcome.

However, this problem can be alleviated to some extent, since with an appropriate software implemented in a controller of the laser beam 40 the transverse displacement of the surgical pattern can be corrected to a reasonable degree. This correction is relatively straightforward as the surgical pattern preserves its essentially constant depth from the corneal surface even after the lateral displacement. Therefore, the controller can correct the displacement by shifting the lateral x and y coordinates of the surgical pattern 50.

The above described case involving a laterally movable PI is but one example of the displacement between the eye and the laser system. The displacement can occur in several others forms for the above PI architectures. For example, for each of the PI architectures, the contact lens may be docked off the center of the eye, causing similar misalignment. Or, the PI 20 and the contact lens 30 can be off-center relative to both the eye 5 and to the distal end 10. A feature shared by all these examples is that the surgical cut may end up shifted from its intended location and pattern, but the shift can be compensated with a relatively straightforward software correction.

FIG. 2B illustrates that the challenge is considerably greater for curved contact lenses. In such systems, if the transversely movable PI 20 is misaligned relative to the distal end 10, then the corneal or radial distance of the displaced surgical pattern is not preserved. In a typical LASIK surgery the corneal cuts or surgical patterns are placed at about 100 microns depth below the corneal surface. Therefore, if the contact lens and thus the surgical pattern are laterally misplaced by 100-200 microns, this can cause the radial distance of the surgical pattern from the corneal surface, the "radial depth" to be reduced by 30-60 microns at some points, placing the cut perilously close to the corneal surface.

The lateral displacement of the surgical pattern is not the only problem: the displaced surgical pattern ceases to run parallel to the corneal surface as well. Therefore, undesirably, the displaced surgical pattern will be formed at an angle to the corneal surface, potentially leading to astigmatisms and other forms of misalignments. One aspect of such misalignments in curved-lens PIs is that they cannot be corrected by a software simply shifting the surgical pattern laterally. Rather, only complex reference measurements and calculations of curved wavefronts can attempt to correct or compensate these misalignments. In particular, even such calculated compensating adjustments cannot undo the generated astigmatism.

Finally, the displacement of the surgical pattern can direct the laser beam beyond the maximal design distance from the center, where the aberration of the laser beam will exceed the design specifications, causing yet another challenge.

In response to these challenges, embodiments of an adjusting ophthalmic docking system can reduce or even eliminate the above problems as described below.

In particular, an implementation of an adjusting ophthalmic docking system can include a curved contact element, configured to be disposed on a procedure eye, a conformation platform at a distal tip of an optical system, configured to support an adjustment of the curved contact element, and a connector, configured to accommodate the adjustment of the contact element.

Some implementations of the ophthalmic docking system can include a curved contact lens, having an index of refraction less than 1.44, to be disposed on a procedure eye, and an adjusting platform coupled to an objective of an optical system to support a rotational adjustment of the curved contact lens.

Some implementations of an ophthalmic docking system can include an ophthalmic laser system having an objective, a patient interface to be connectable to the objective, and having a contact lens, and a circular support element, attached to the objective, to support a rotation of the contact lens relative to the objective.

Some embodiments of an ophthalmic docking system can include a surgical laser having a procedure end, and a contact element, disposable on a procedure eye and rotatably coupled to the procedure end of the surgical laser.

BRIEF DESCRIPTION OF THE DRAWINGS

FIGS. 2A-B illustrate contact lenses docked centrally on the eye but displaced from the axis of the laser system.

FIGS. 3A-C illustrate embodiments of adjusting ophthalmic docking systems aligned and displaced from the laser system.

FIGS. 4A-B illustrate various architectures of the connector or enabler.

DETAILED DESCRIPTION

Implementations and embodiments described in this patent document offer improvements for the above described challenges caused by possible displacements and misalignments between the docked contact lenses, the procedure eye and the ophthalmic laser systems.

Figure 3A:
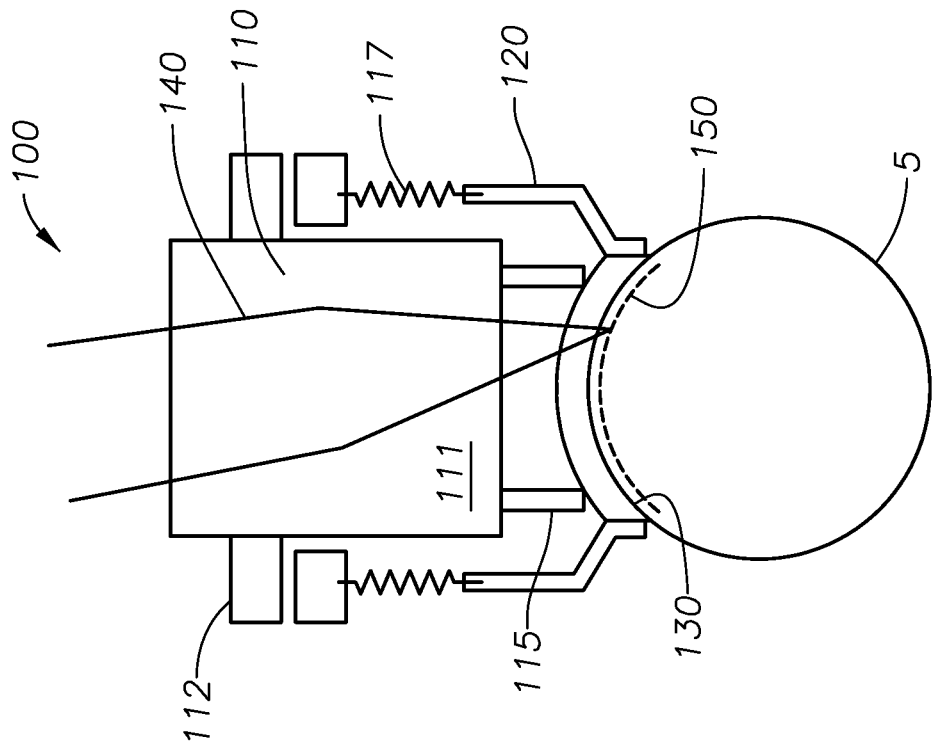

FIG. 3A illustrates an adjusting ophthalmic docking system 100 that includes a distal end 110 of an optical system, a patient interface 120 and a curved contact element, or contact lens 130, configured to be disposed on the procedure eye 5. In some references the contact element 130 is referred to as an applanation plate even if it has a curvature. As before, the docking system 100 can be configured to guide a laser beam 140 of the optical system into the eye 5 according to a surgical pattern 150 in order to form a surgical cut. The distal end 110 can include an objective 111 and a connecting flange 112. The surgical pattern 150 can be referenced to the contact element 130, to the objective 111 or to an internal reference of the docking system 100. The contact element 130 can be part of the patient interface 120 and the patient interface 120 can be removably connectable to the docking system 100. The patient interface 120 can be any of the above described three types of patient interfaces: a one piece PI, a two or multiple piece PI, or a laterally movable PI, or can have other implementations.

In addition, the docking system 100 can include a conformation platform 115 at a distal tip of the distal end 110, configured to support an adjustment of the contact element 130. The docking system 100 can also include a connector 117, configured to accommodate the adjustment of the contact element 130.

In some embodiments, the conformation platform 115 can be configured to support a rotational adjustment of the contact element 130. This is a functionality beyond the above described three types of PIs that are either tightly connected to the distal end 110 of the laser system, or can accommodate a transverse or lateral displacement only.

FIGS. 3B-C illustrate that the conformation platform 115 can be configured to movably contact the contact element 130 via a cylindrical distal end. This distal end can be a ring or a cylinder. In some cases, the conformation platform 115 can include an annular segment of a sphere.

FIGS. 3B-C illustrate that the embodiments of the conformation platform 115 are capable of supporting a rotation of the curved contact element 130, shown with the solid arrow. This functionality can increase the precision of docking in the adjusting docking system 100 having the curved contact lens 130, since if the curved contact lens 130 is not centered or aligned with the objective 111 then this misalignment cannot be compensated by a lateral movement of the PI 120 alone, the maximum adjustment allowed by earlier PI systems.

In detail, FIGS. 3B-C illustrate a docking process misaligning the curved contact lens 130 relative to the objective 111. As discussed above, misalignment can arise for at least two reasons: prior to the docking the PI 120 may have been attached to the distal end 110 off-center, or during docking the curved contact lens 130 may have been centered with an eye 5 whose center 5c was not centered with that of the objective 111 or whose optical axis 5a (dashed line) was not aligned with an optical axis 111a of the objective 111 (dotted line), the example shown in FIG. 3B.

FIG. 3C illustrates that as the curved contact lens 130 of the adjusting docking system 100 is lowered onto an off-center eye 5, the curved contact lens 130 can accommodate or compensate this lack of centration and alignment by performing a rotation, possibly combined with a lateral shift. The rotation is exaggerated by the solid arrow for emphasis. The conformation platform 115 and the connector 117 are elements that make such a rotational accommodation possible. In some embodiments, the ring shape of the conformation platform 115 makes it possible that the curved contact lens 130 can maintain its conformation to the conformation platform 115 even during a misaligned and non-centered docking procedure. In this sense, PI 120 can be called a conforming PI 120 or a conformation-preserving PI 120.

The flexibility of the connector 117 can further assist maintaining contact and conformation between the conformation platform 115 and the curved contact lens 130. In some implementations, the connector 117 can include a flexible element, an elastic element, a magnetic coupling element, a vacuum-suction element, a gravitational connector, a frictional connector or a viscous connector.

In embodiments, the adjusting ophthalmic docking system 100 can have a sufficiently soft connector 117 that allows the adjustment of the curved contact lens 130 upon docking with a misaligned eye. In other embodiments, the connector 117 can be sufficiently hard to allow for an adjustment of the curved contact lens 130 when attached to the objective in a misaligned position prior to the docking.

The benefits of the adjusting docking system 100 include the followings. (i) The rotated and possibly laterally shifted contact lens 130 can dock on a misaligned and non-centered eye while causing only reduced deformation and wrinkling of the cornea. (ii) The rotation and possible shift of the contact lens 130 may guide the misaligned and non-centered eye and the distal end 110 to reduce their relative displacement and misalignment during the docking procedure. (iii) The rotation and possible shift of the curved contact lens 130 can compensate a misaligned or non-centered pre-procedure attachment of the PI 120. (iv) Since the top or proximal surface of the contact lens 130 is curved with a comparable or equal radius of curvature as its bottom or distal surface, the contact lens 130 appears optically unchanged after its rotation, while its contact and conformity to the conformation platform 115 is maintained. Thus, the optical path of the laser beam 140 is also unchanged by the rotation. Therefore, the computation of the surgical pattern 150 to be followed by the laser beam 140 does not need to account for or modified by the rotation of the contact lens 130. (v) Finally, no additional or enhanced aberration is generated by the displacement and subsequent rotation between the contact lens 130 and the distal end 110.

The above benefits of the conforming PIs 120 can be compared to docking systems that do not allow the rotational conformation of a curved contact lens to their platform, only a lateral shift, the docking system 1 being an example. When such systems face a misaligned docking, (i) the cornea may be deformed or wrinkled excessively; (ii) the misalignment does not get reduced during the docking procedure; (iii) a PI, attached to the objective with a misalignment, cannot be righted by a lateral shift alone; (iv) if the contact lens is shifted to compensate for a misalignment, it may appear different for the laser beam, thus modifying the optical path of the beam, leading to beam-pointing errors; and finally, (v) an induced lateral shift of the contact lens can lead to an enhancement of the aberration of the laser beam.

These characterizations are meant within reasonable tolerances of the system. For example, some existing docking systems may have a positional uncertainty along the optical axis, z direction, or longitudinal direction, caused, e.g., by the imprecision of manufacturing. This uncertainty and possibly corresponding PI movement can be of the order of 10 microns or more. However, while these PIs may accommodate some longitudinal movement, this movement or tolerance is neither controlled nor utilized to correct the misalignment or non-centeredness of the contact element 130. As such, these PIs are correctly characterized as non-conforming PIs that accommodate only lateral displacements in a controlled manner.

Accommodating displacements with rotational and translational movement can reduce the variation of the (radial) depth of the surgical cuts, one of the challenges of the rigid or only laterally movable PIs with a curved contact lens. As before, the radial depth here refers to the radial distance of the cut from the surface of the cornea. In implementations of the docking system 100, the conformation platform 115 and the connector 117 can be configured such that the optical system having the adjusting docking system 100 is capable of forming a corneal flap-cut with a radial depth between 50 microns and 200 microns even when the contact element 130 is docked on the procedure eye 1 mm from a center of a limbus of the eye. In some implementations, the corneal flap-cut can be formed with a radial depth between 70 microns and 130 microns when the contact element 130 is docked on the procedure eye 1 mm from the center of the limbus. Here, an example of the corneal flap-cut is a full circular flap-cut of a LASIK procedure, typically formed in a radial depth of about 100 microns. The flap-cut is typically formed with a flap hinge.

Implementations of the docking system 100 can also reduce the angle between the flap-cut and the corresponding corneal surface element to less than 1 milliradian when the contact element 130 is docked on the procedure eye 1 mm from the center of the limbus. In some implementations, this angle can be reduced to less than 0.5 milliradian. Here, the "corresponding surface element" can refer to the corneal surface element that is pierced by a radial ray pointing from the center of the eye-globe to the surgical cut element.

FIGS. 4A-B illustrate that several different implementations of the ophthalmic system 100 can provide similar functionalities. FIG. 4A illustrates that the connector 117 can be based at the distal end 110 of the optical system. The connector 117 can include a flexible element 117-1 and a connector element 117-2. The connector element 117-2 can be connectable to the patient interface 120 and the flexible element 117-1 can be anchored at the connecting flange 112.

FIG. 4B illustrates that some implementations of the connector 117 can be part of the patient interface 120. These implementations of the connector 117 can include the flexible element 117-1 and a connector element 117-3 that can be connected to the distal end 110 of the optical system, typically to its connecting flange 112.

As described above, the adjustable docking system 100 can be implemented in several other ways as well. For example, in a two-piece PI the top part, the bottom part, or both parts of the two-piece PI can include a flexible element. In another two-piece PI design, the connection between the top part and the bottom part of the PI can be flexible. Further, in a laterally movable PI the top portion of the PI can be laterally movable while the bottom part can have a flexible element. Finally, the flexible element can have many different implementations as well, a flexible or accordion-like z-directional tube, or flexible bayonet flanges in the x-y plane, or elastic walls for the PI 120, among others.

The above implementations of the adjusting docking system 100 offer partial compensation and solution for the problems arising from a misaligned docking of a curved contact lens, including (i) the displaced surgical patterns, (ii) the varying cutting depth, and (iii) the varying cutting angle.

These problems can be further reduced or alleviated by implementing an adaptive software in a controller of the optical system. The controller can determine and analyze the misalignment between the eye and the distal end e.g. by analyzing an image of the eye after docking. Part of the analysis can be carried out by an operator of the system, for example, by a surgeon moving markers on an electronic image. The image can be generated by electronic imaging of the eye or by performing an Optical Coherence Tomographic (OCT) imaging. Based on this analysis, the controller can adopt offsets when driving optical scanners that deflect and scan the laser beam according to the surgical pattern to compensate the misalignments in all three dimensions and place the surgical pattern into its intended location. These offsets can be implemented either as analog signals or digitally by software solutions.

In addition to the above three problems (i)-(iii), curved contact lenses can cause excess aberration because the laser beam 140 traverses the surfaces of the contact lens 130 at a relatively steep angle, especially at the periphery of the contact lens 130. The optical design of the ophthalmic docking system 100 can minimize aberrations at the patient interface 120 and at the eye 5 for their nominal, centered position relative to the objective 111. However, additional non-compensated aberrations can occur if the patient interface 120 or the eye 5 is misaligned or non-centered relative to their nominal position.

In contrast to the above three problems of controlling the placement, depth and angle of the cuts in the eye, controlling the excess aberration caused by a misalignment or non-centeredness of the curved contact lens 130 cannot be achieved fully by using an adjusting docking system or by software solutions, and thus remains a challenge.

Figure 1A:
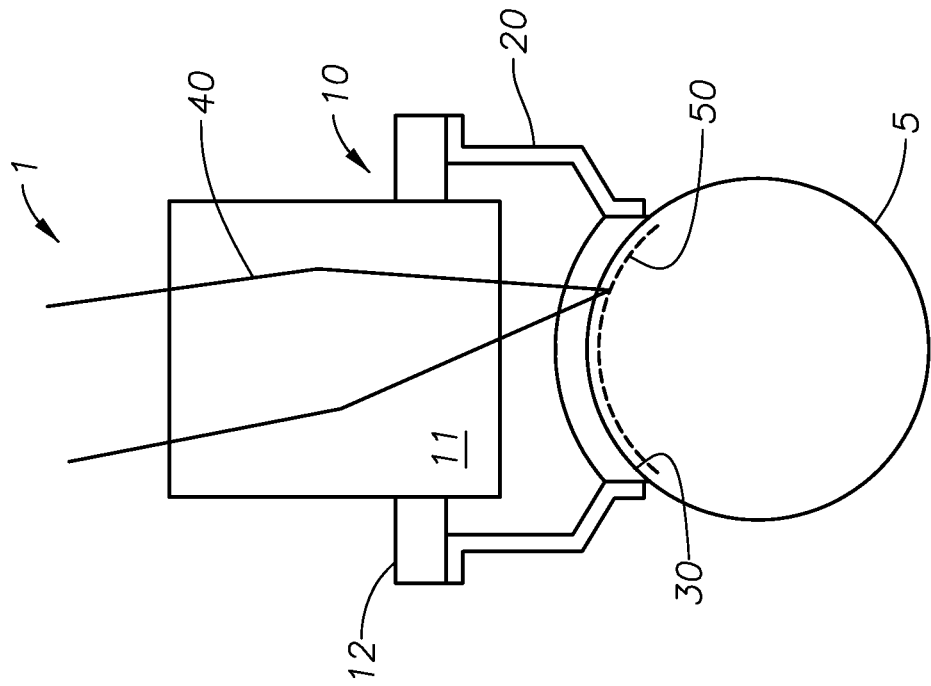
FIGS. 1A-B illustrate contact lenses docked centrally on the eye and aligned with the laser system.
Figure 1B:
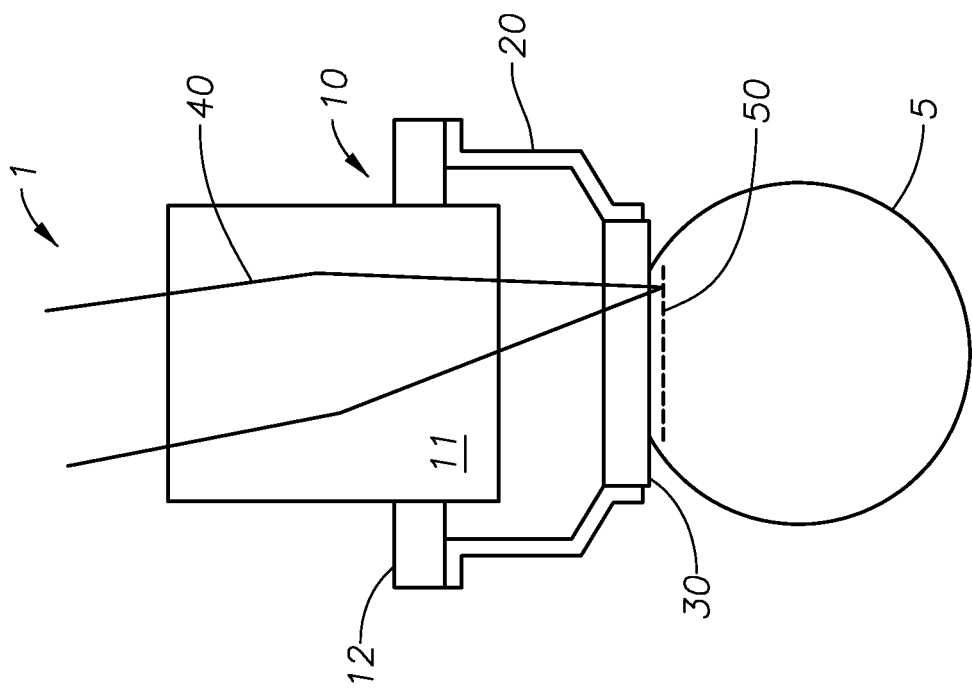
Figure 5A:
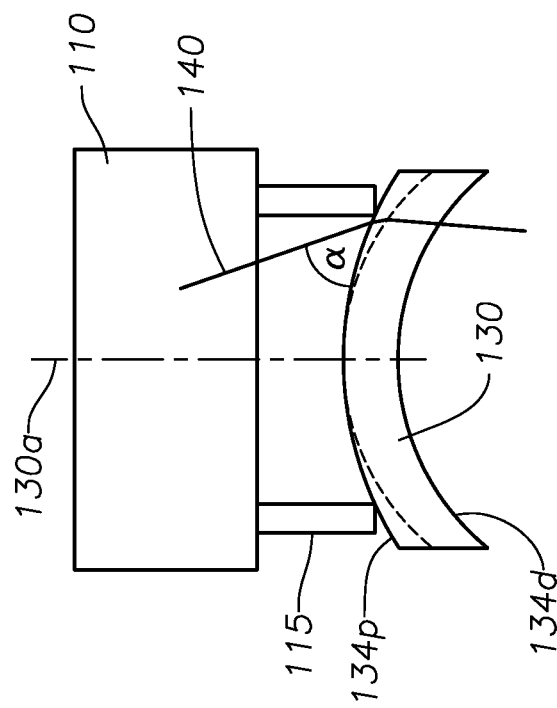
FIGS. 5A-C illustrate meniscus-shaped contact lenses with different proximal and distal radii.

FIG. 5A illustrates an embodiment that offers added control of the aberration caused by a misaligned curved contact lens 130. In this embodiment, the contact lens 130 may be a meniscus-shaped contact lens 130 with a proximal surface 134p with a radius Rp and a distal surface 134d with a radius Rd, the two radii not necessarily equal to each other.

Implementations of the adjusting ophthalmic docking system 100 can reduce the excess aberration by employing a proximal radius Rp that is greater than the distal radius Rd, since the proximal surface of such lenses are flatter, reducing the steepness of the incident angle α at the periphery of the lens 130, while still maintaining a full, non-deforming contact with the cornea whose radius is smaller than Rp.

These implementations also ensure that the proximal surface 134p of the contact lens 130 stays aligned with the objective 1110 through contact to the conformation platform 115. Further, the meniscus shaped contact lens 130 minimizes the misalignment of the distal surface 134d during a "sliding" rotational misalignment of the lens on the conformation platform 115.

This aberration control can be achieved at a limited "cost" by using a material for the meniscus-shaped contact lens 130 with an index of refraction n(meniscus) close to that of the cornea, n(cornea)=1.38, approximately. In the particular case of n(meniscus)=n(cornea), the laser beam does not experience any refraction at the distal surface 134d, thus avoiding the creation of additional aberration. For contact lenses 130 with n(meniscus) close to n(cornea), the refraction and the corresponding generated aberration is proportional to the difference of the indices of refraction [n(meniscus)−n(cornea)] and thus remains small.

The index of refraction of some embodiments of the meniscus-shaped contact lens 130, n(meniscus), can be less than 1.55. In others, n(meniscus) can be less than 1.44. Some of the commercial optical glasses can have an index of refraction as low as 1.44, creating an index difference of [n(meniscus)−n(cornea)]=0.06. In yet other embodiments, the meniscus-shaped contact lens 130 can be fabricated from a fluoro-polymer. Such contact lenses can reduce the index-of-refraction difference [n(meniscus)−n(cornea)] below 0.06 potentially even eliminating the difference entirely. Embodiments of the contact lens 130 made of a fluoro-polymer are generally advantageous for aberration control, regardless of the relative tilt or misalignment.

Figure 5C:
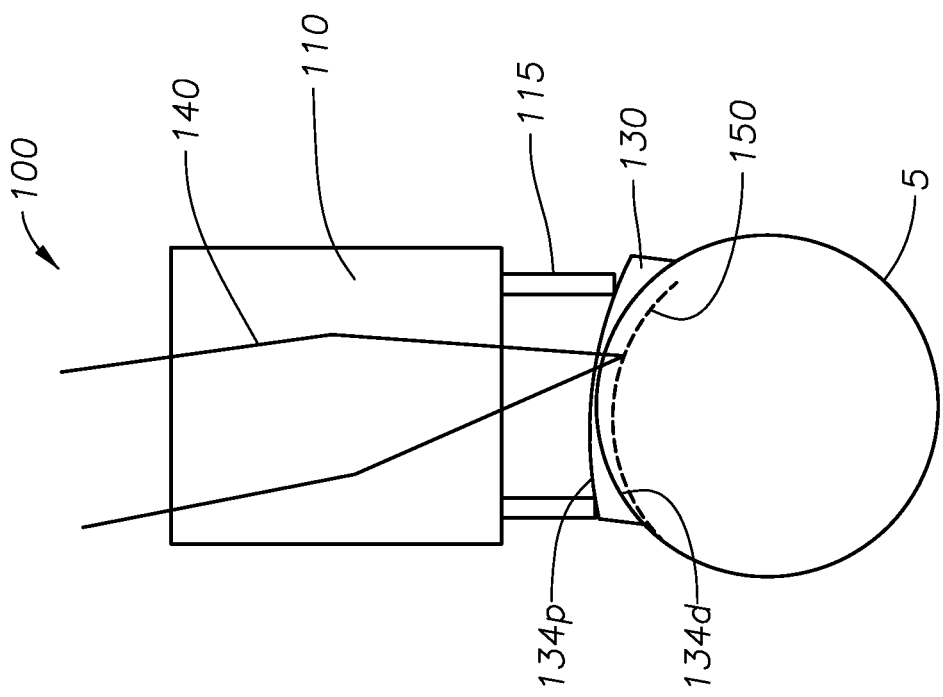
Figure 5B:
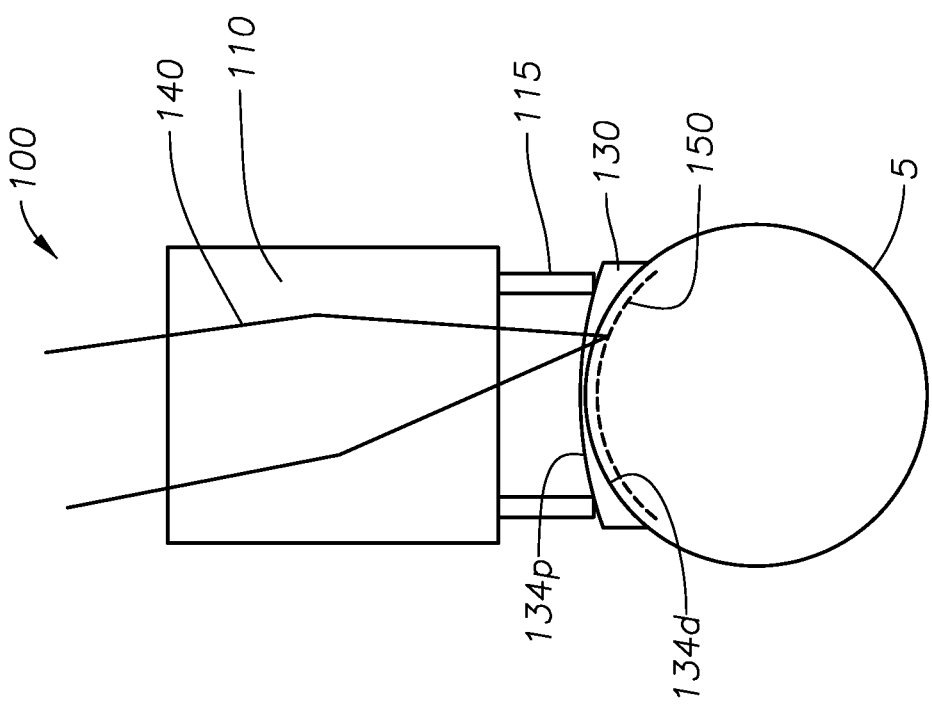

FIGS. 5B-C illustrate another aspect of these meniscus-shaped contact lenses 130. When the meniscus-shaped contact lens 130 is docked in a misaligned position, as in FIG. 5C, it adapts and accommodates to the misalignment by a rotation, as shown.

While the rotated proximal surface 134p will appear unchanged for the incident laser beam 140 However, the rotated distal surface 134d will appear rotated and displaced for the laser beam 140 because the two surfaces 134p and 134d in general do not share a common center. Therefore, the surgical pattern 150 can be shifted from its intended position by the rotation of the meniscus-shaped contact lens 130, as shown in FIG. 5C.

Therefore, the parameters of the meniscus-shaped contact lens 130, such as Rd, Rp, n(meniscus) and a lens-thickness D can be selected to balance the gain in aberration control against the unwanted shift of the surgical pattern. For example, the lens thickness D can be selected to move the centers of the distal and proximal surfaces 134d and 134p closer to each other. In some concentric implementations D can even assume a value which makes the two centers coincide, completely eliminating the unwanted shift of the surgical pattern. In terms of the lens thickness D and the two radii, this condition of concentricity can be expressed as Rp=Rd+D.

Concerning the values of the radii, in some meniscus-shaped contact lenses 130 Rd can be less than 20 mm. In others, less than 15 mm. In yet others, 10 mm. These radius values are close to the typical corneal radius of about 7.5-8 mm and thus reduce the possible wrinkling and other deformations caused by the docking of the contact lens 130.

The aberration can have different types, including spherical aberrations, coma, astigmatism, field curvature and distortion. These aberrations can be quantified in several different ways, including the $a_{mn}$ aberration coefficients, the $r_f$ radius of focal spot, the S Strehl ratio, and ω, the root-mean-square, or RMS, wavefront error. All these terms have well established meaning in the art.

Implementations of the adjusting docking system 100 can be configured such that at least one of the above aberration measures of the laser beam 140 varies less than 10 percent within a central circle of radius of 2 mm when the contact lens 130 is attached to the objective 111 off-center by 1 mm.

Some embodiments of the adjusting ophthalmic docking system 100 can have a "flex-and-lock" mechanism: they can include the connector 117 with a flexible element 117-1, where the flexible element 117-1 can allow the contact lens 130 to rotatably adjust if the contact lens 130 was not properly aligned with the objective 111. Once, however, the operator of the system, such as the surgeon, determines that the contact lens 130 has been properly aligned with the objective 111 then the flex-and-lock can be locked down, inhibiting further movement of the contact lens 130 relative to the objective 111, thus preserving their alignment.

Some adjusting ophthalmic systems can include an ophthalmic laser system with an objective, a patient interface that is connectable to the objective and includes a contact lens, and a circular support element, attached to the objective to support a rotation of the contact lens relative to the objective.

Some of these ophthalmic systems can include an enabler, enabling the rotation of the contact lens, where the enabler can be a flexible element, an elastic element, a magnetic coupling element, a vacuum-suction element, a gravitational connector, a frictional connector or a viscous connector.

The enabler can be a part of the patient interface or can be a connector between the patient interface and the objective.

Some ophthalmic systems can include a surgical laser having a procedure end and a contact lens rotatably coupled to the procedure end of the surgical laser. The contact lens can have a proximal and a distal surface, the distal surface having a smaller radius than the proximal surface.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:

1. An adjusting ophthalmic docking system, comprising:
    a curved contact element, configured to be disposed on a procedure eye;
    a conformation platform at a distal tip of an optical system, configured
        to support an adjustment of the curved contact element, and
        to movably contact the contact element via at least one of a cylindrical distal end and an annular sphere-segment; and
    a connector, configured to accommodate the adjustment of the contact element.

2. The adjusting ophthalmic docking system of claim 1, wherein:
    the conformation platform is configured to support a rotational adjustment of the contact element.

3. The adjusting ophthalmic docking system of claim 2, wherein:
    the conformation platform is configured to support a translational adjustment of the contact element.

4. The adjusting ophthalmic docking system of claim 1, wherein:
    the connector comprises at least one of
        a flexible element, an elastic element, a magnetic coupling element, a vacuum-suction element, a gravitational connector, a frictional connector and a viscous connector.

5. The adjusting ophthalmic docking system of claim 1, wherein:
    the conformation platform and the connector are configured such that the optical system having the adjusting docking system is capable of forming a corneal cut with a radial depth between 50 microns and 200 microns when the contact element is docked on the procedure eye 1 mm from a center of a limbus of the eye.

6. The adjusting ophthalmic docking system of claim 1, wherein:
    the conformation platform and the connector are configured such that the optical system having the adjusting docking system is capable of forming a corneal cut with a radial depth between 70 microns and 130 microns when the contact element is docked on the procedure eye 1 mm from a center of a limbus of the eye.

7. The adjusting ophthalmic docking system of claim 1, wherein:
    the conformation platform and the connector are configured such that the optical system having the adjusting docking system is capable of forming a corneal cut with angle of less than 1 milliradian relative to a corresponding surface element of the procedure eye when the contact element is docked on the procedure eye 1 mm from a center of a limbus of the eye.

8. The adjusting ophthalmic docking system of claim 1, wherein:
    the conformation platform and the connector are configured such that the optical system having the adjusting docking system is capable of forming a corneal cut with angle of less than 0.5 milliradian relative to a corresponding surface element of the procedure eye when the contact element is docked on the procedure eye 1 mm from a center of a limbus of the eye.

9. The adjusting ophthalmic docking system of claim 1, wherein:
    the curved contact element is part of a patient interface.

10. The adjusting ophthalmic docking system of claim 9, wherein:
    the connector is connectable to the patient interface.

11. The adjusting ophthalmic docking system of claim 9, wherein:
    the connector is part of the patient interface.

12. The adjusting ophthalmic docking system of claim 1, wherein:
 the patient interface is one of a one-piece patient interface, a multi-piece patient interface and a laterally movable patient interface.

13. The adjusting ophthalmic docking system of claim 1, the contact element comprising:
 a meniscus-shaped lens, having
  a proximal surface with a first radius; and
  a distal surface with a second radius, wherein the second radius is smaller than the first radius.

14. The ophthalmic docking system of claim 13, wherein:
 the proximal surface and the distal surface are concentric.

15. The adjusting ophthalmic docking system of claim 14, wherein:
 the second radius is less than 20 mm.

16. The adjusting ophthalmic docking system of claim 14, wherein:
 the second radius is less than 15 mm.

17. The adjusting ophthalmic docking system of claim 1, the curved contact element comprising:
 an optically transmissive lens, having an index of refraction less than 1.55.

18. The adjusting ophthalmic docking system of claim 1, the curved contact element comprising:
 an optically transmissive lens, having an index of refraction less than 1.44.

19. The adjusting ophthalmic docking system of claim 1, the curved contact element comprising:
 an optically transmissive lens, comprising a fluoro-polymer.

20. The adjusting ophthalmic docking system of claim 1, wherein:
 the optical system is configured such that an aberration measure of a laser beam of the optical system varies less than 10 percent within a circle of radius of 2 mm when the curved contact element is attached to the optical system 1 mm off-center.

21. The ophthalmic docking system of claim 1, comprising:
 a lock, lockable to hold the curved contact lens fixed relative to the distal tip of the optical system.

* * * * *